United States Patent [19]

Rao

[11] Patent Number: 4,748,854
[45] Date of Patent: Jun. 7, 1988

[54] FATIGUE TEST APPARATUS
[75] Inventor: Dantam K. Rao, West Carrollton, Ohio
[73] Assignee: Systran Corporation, Dayton, Ohio
[21] Appl. No.: 922,627
[22] Filed: Oct. 24, 1986

Related U.S. Application Data
[63] Continuation-in-part of Ser. No. 873,225, Jun. 10, 1986, abandoned.
[51] Int. Cl.⁴ ............................................. G01N 3/32
[52] U.S. Cl. ........................................ 73/799; 73/837
[58] Field of Search ................. 73/799, 798, 797, 796, 73/794, 802, 808, 837

[56] References Cited

U.S. PATENT DOCUMENTS

| | | | |
|---|---|---|---|
| 1,583,877 | 5/1926 | Hahnemann et al. | 73/797 |
| 2,137,852 | 11/1938 | Nicolson | 73/773 |
| 2,693,699 | 11/1954 | Federn | 73/797 |
| 2,824,594 | 2/1958 | Gray | 73/837 |
| 3,442,120 | 5/1969 | Russenberger et al. | 73/808 |
| 4,283,956 | 8/1981 | Lechner et al. | 73/799 |

FOREIGN PATENT DOCUMENTS 1065722  1/1984  U.S.S.R. .......................... 73/799

Primary Examiner—Stewart J. Levy
Assistant Examiner—Robert R. Raevis
Attorney, Agent, or Firm—Biebel, French & Nauman

[57] ABSTRACT

A fatigue test apparatus in which a specimen to be tested is attached at its ends to a pair of opposing pistons positioned within a pair of opposing cylinders. The cylinders are attached to a support frame such that the specimen is oriented substantially vertically. In a preferred embodiment, the specimen is enclosed in a heat chamber to test at high temperatures. Each of the pistons is attached to a shaft having a weight at its end and the weights are drivingly connected to a pair of shakers which are actuated to vibrate 180° out of phase with each other. The cylinders are pressurized to exert a static tensile load on the specimen, and the shakers are actuated to exert a dynamic tensile load which is superimposed on the static load and travels through the weights, shafts and pistons to the specimen. With this arrangement, the dynamic load is not transmitted to the support frame so that the vibration characteristics of the support frame do not affect the vibration behavior of the specimen, yielding a dynamic load source independent of static or thermal load sources, more accurate results. By varying the magnitude of the weights and the stiffness characteristics of the shafts, static, dynamic or thermal fatigue tests may be conducted on a specimen either singely or in any combination with dynamic loads imposed at frequencies as high as 10,000 Hz.

21 Claims, 2 Drawing Sheets

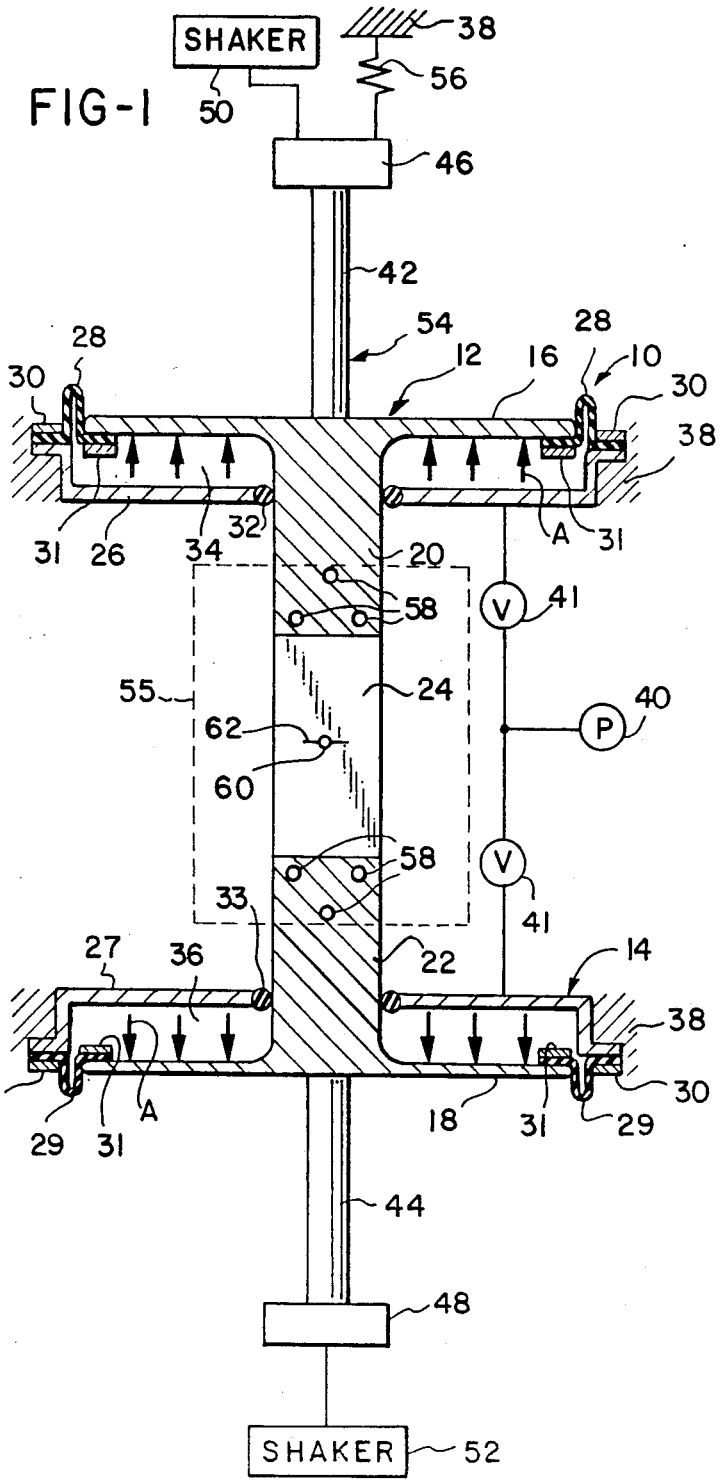

FATIGUE TEST APPARATUS

This invention was made with Government support under contract F33615-84-6-5116 awarded by the U.S. Air Force. The Government has certain rights in this invention.

CROSS REFERENCE TO RELATED APPLICATION

This application is a continuation-in-part of U.S. application Ser. No. 873,225 filed June 10, 1986, now abandoned.

BACKGROUND OF THE INVENTION

The present invention relates to testing apparatus, and more particularly to fatigue testing apparatus in which a specimen is subjected to both a static and dynamic load for crack initiation and crack propagation studies.

Many types of machinery include components which must withstand cyclical stressing at high speeds. For example, an aircraft jet engine includes rotating components such as turbine blades and discs which rotate at thousands of revolutions per minute. Such components are subjected to low cycle, mostly static stresses due to centrifugal forces and high cycle, mostly dynamic stresses due to resonance responses at high frequencies, as well as thermal excursions. These thermo-mechanical loads can initiate or propagate cracks at preexisting defects or scratches, and thereby reduce the fatigue life of the components.

In actual use, typical aircraft engine blade or disc materials may be subjected to static and dynamic stresses of 100,000 psi and 20,000 psi, respectively, due to centrifugal and resonance effects. The dynamic stresses might occur at any potential resonance frequency, from 100 Hz for long fan blades to 5,000 Hz for short turbine blades to 10,000 Hz for ultrashort engine blades of the type used on the space shuttle. Accordingly, there is a need for test systems which can impose both low frequency and high frequency loads on a specimen simultaneously.

Various devices have been developed to impose both static and dynamic loads upon a specimen. For example, in one device a specimen is attached at one end to a support frame and at its other end to a high capacity electrodynamic snaker which generates a high cycle load. The shaker is attached to a servohydraulic system which develops a low cycle load, and an intermediate rubber isolator is included in the connection between the shaker and servohydraulic system to prevent transmission of high cycle vibrations generated by the shaker back to the servohydraulic system.

In another device, a specimen is attached at one end to a support frame and at its other end to the rod of a piston within a cylinder pressurized by compressed air which exerts the low cycle load. A shaker is directly coupled to the piston and exerts the high cycle load.

A disadvantage with both of the aforementioned systems is that they have limited frequency capability and nonlinear calibration characteristics beyond approximately 1,000 Hz, and the latter system experiences a high cycle load capacity drop at frequencies higher than about 1,000 Hz. Furthermore, with an upper limit of about 1,000 Hz, it would take almost three hours to complete a ten million cycle test.

Another disadvantage with the aforementioned devices is that in both, the specimen is rigidly attached at one end to the support frame. Consequently, the imposition of high frequency stressing on the specimen causes the frame to vibrate along with the specimen and thereby affects the accuracy of the testing of the specimen. Furthermore, in crack propagation studies, the growth of the crack in the specimen affects the resonant frequency of the specimen and thereby changes the resonant characteristics of the entire system. This, too, affects the overall accuracy of the testing.

An additional disadvantage with the aforementioned devices is that, if the specimen tested is to be subjected to thermal loads by enclosing it in a furnace, a closed loop computer control is necessary to continuously adjust the position of the servohydraulic piston to maintain constant load on the specimen independently of the effects of thermal expansion. Consequently, the need for placing sensors on the apparatus within the furnace would greatly complicate the system.

Accordingly, there is a need for a fatigue testing apparatus in which both the specimen and the components exerting the high and low cycle loads are isolated from the support frame so that the support frame does not affect the dynamic characteristics of the load train. Furthermore, there is a need for a testing apparatus in which high cycle loads in excess of 1,000 Hz can be imposed upon a specimen, simultaneously with low cycle static loads, and yield accurate results which are substantially unaffected by changes in resonance frequency of a specimen caused by crack propagation.

SUMMARY OF THE INVENTION

The present invention is a high frequency fatigue test apparatus which can subject a specimen to both a static low cycle load and a dynamic high cycle load, and in which the high cycle loading is isolated from the support frame. The apparatus is capable of applying static, dynamic or thermal loads independently or in any specified combination. Furthermore, the apparatus compensates for the changes in the resonant frequency of the specimen which naturally occur during crack propagation testing.

The apparatus is also adjustable to provide accurate high cycle loading at frequencies of up to 10,000 Hz. Consequently, a ten million cycle test can be completed in as little as seventeen minutes.

The invention includes a support frame, upper and lower cylinder actuators attached to the frame and adapted to clamp to the ends of a test specimen, upper and lower shafts attached to the upper and lower actuators, respectively, upper and lower weights attached to the shafts, and a shaker attached to at least one of the weights. The cylinder actuators each include a cylinder rigidly attached to the frame, a piston connected to the cylinder by a flexible diaphragm and a rod attachable to an end of the specimen. Seals between the rods and cylinders, together with the diaphragms, form an airtight chamber within each cylinder.

The pistons, shafts, weights, and specimen together form an elongated load train which is suspended vertically from the frame by a spring attached to the upper weight. The specimen portion of the apparatus may be enclosed in a thermal chamber to test at elevated temperatures. Since the load train is attached to the frame only by the spring, flexible diaphragms and seals, the behavior of the load train in response to the high cycle loading imposed by the shaker is unaffected by the masses and stiffnesses of the frame or cylinders. A static load is imposed on the specimen by pressurizing the chambers of the cylinder actuators, which are oriented to oppose each other and exert a tensile or compressive load on the specimen gripped between them.

In tne preferred embodiment, the weights are attached to their respective pistons by shafts which have a stiffness or spring constant such that the natural frequency of the load train equals or is a harmonic of the desired high cycle frequency. Consequently, a relatively small driving force can cause a relatively large oscillation of the specimen.

For crack propagation tests, the shafts are selected so that their spring constants causes the load train to vibrate in response to the driving frequency of the shaker, such that there are oscillation nodes (points of no oscillation) at the center of the specimen and at a point along each of the shafts very close to the pistons. The result is that the portion of the train extending between the center of the specimen and the nodes located on the shafts has an effective stiffness which is only slightly affected by a change in stiffness of the specimen as the crack propagates. Consequently, the apparatus generates a steady high cycle load which is independent of the duration of the test of the specimen.

For crack initiation tests, in which a specimen without a starter crack is cyclically stressed until a crack forms, shaft dimensions and driving frequency are selected so that there is a single node which coincides with the center of the specimen.

Accordingly, it is an object of the present invention to provide an apparatus for fatigue testing a specimen in which both high cycle, low cycle, and thermal loads are imposed on a specimen either independently or simultaneously; an apparatus in which a load train free at both ends automatically induces a constant load on a specimen, without need of computer control to compensate for thermal expansion; an apparatus in which the load train is symmetric about the center of the specimen so a starter crack grows symmetrically; an apparatus in which pneumatic cylinders cushion the load train symmetrically and reduce alignment problems; an apparatus in which a high cycle load may be imposed on a specimen which is isolated from and unaffected by supporting structure; an apparatus in which the high cycle resonant frequency is not appreciably shifted by crack propagation in the specimen, so that a lighter duty shaker can be used for a given high frequency load; and an apparatus in which relatively small shakers are used to impose a relatively large dynamic load upon a specimen, thereby minimizing the overall cost of the apparatus.

Other objects and advantages of the invention will be apparent from the following description, the accompanying drawings, and the appended claims.

BRIEF DESCRIPTION OF THE DRAWINGS

FIG. 1 is a schematic diagram of a preferred embodiment of the present invention, set up to perform a crack propagation test;

DETAILED DESCRIPTION OF THE PREFERRED EMBODIMENT

Figure 3:
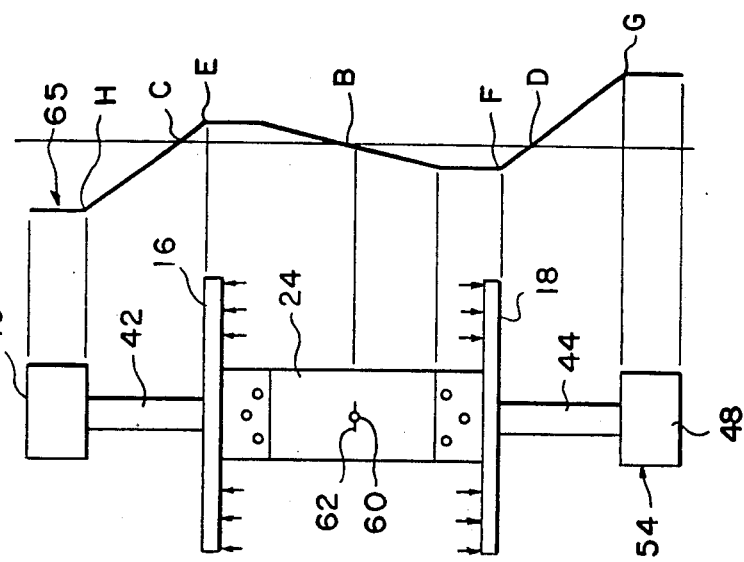
FIG. 3 is a schematic representation of the embodiment of FIG. 1, including a graph of the maximum amplitude of longitudinal vibration of each component of the apparatus and specimen, set up to perform a crack propagation test.

As shown in FIG. 1, the test apparatus of the present invention, generally designated 10, includes upper and lower cylinder actuators 12, 14. The actuators 12, 14 include pistons 16, 18, respectively, having rods 20, 22 adapted to grip a specimen 24. The pistons 16, 18 are slidably mounted within upper and lower cylinders 26, 27. The cylinders 26, 27 include flexible, annular diaphragms 28, 29 which extend between the cylinder walls and pistons and are secured thereto by rings 30, 31, respectively. O-ring seals 32, 33 extend between the rods 20, 22 and cylinders 26, 27, respectively. The pistons, 16, 18, cylinders 26, 27, diaphragms 28, 29, and seals 32, 33 form airtight chambers 34, 36.

The cylinders 26, 27 are rigidly attached to a support frame 38 of conventional design. The chambers 34, 36 are each connected to a source 40 of compressed air which is regulated by valves 41 to set pressure within the chambers to a predetermined level.

The pistons 16, 18 are connected to shafts 42, 44 which, in turn, are connected to weights 46, 48. Upper and lower shakers 50, 52 are drivingly connected to the weights 46, 48, respectively. In the preferred embodiment, the shakers 50, 52 are model PM50 shakers manufactured by MB Dynamics, Inc., Cleveland, Ohio, and are capable of delivering a fifty pound load. However, it is within the scope of the invention to drive the system with shaker 52 alone.

The weights 46, 48, shafts 42, 44, pistons 16, 18, rods 20, 22, and specimen 24 together comprise a load train 54 which is oriented vertically within the frame 38. In order to compensate for the weight of the train 54, it is suspended from the frame 38 by a suspension means e.g. a soft spring 56 which is attached at its lower end to the upper weight 46.

The apparatus 10 may incorporate a heating chamber 55 which encloses the specimen 24 and parts of the rods 20, 22. Thus, the specimen can be heated to a predetermined temperature during application of the vibrating force. An appropriate chamber is a Lindburg Nichrome chamber. Furthermore, this arrangement eliminates the need for a closed loop computer control to adjust the tension to be applied to the specimen 24, since the specimen is allowed to expand longitudinally.

In operation, the specimen 24 is attached to the rods 20, 22 of the upper and lower cylinder actuators 12, 14 in a conventional fashion by gripping means, such as by bolts, shown schematically as 58. The apparatus 10 shown in FIG. 1 is set up to perform a crack propagation test, so it includes a specimen 24 having starter central hole 60 and starter crack 62 at a midlength.

The chambers 34, 36 are pressurized by the source 40 of compressed air, thereby urging the pistons 16, 18 away from each other in the directions of arrows A and exerting a static tensile load on the specimen 24. The shakers 50, 52 are acutated to impart a cyclical or sinusoidal high frequency dynamic load upon the specimen 24 and are operated so each provides a cyclical variation in force that is 180° out of phase with the other. The excitation force generated by the shakers 50, 52 is transmitted through the weights 46, 48 and along the train 54 to the specimen 24.

This vibratory force is amplified by operating the entire load train 54 at its resonance frequency (a one-node mode for crack initiation tests and a three-node mode for crack propagation tests). The vibrations are not transmitted to the frame 38 through the train 54 since the pistons 16, 18 are isolated from their respective cylinders 26, 28 by the diaphragms 28, 29 and seals 32, 33. However, it should be noted that the static load exerted by the cylinder actuators 12, 14 is transmitted to the frame 38.

Figure 2:
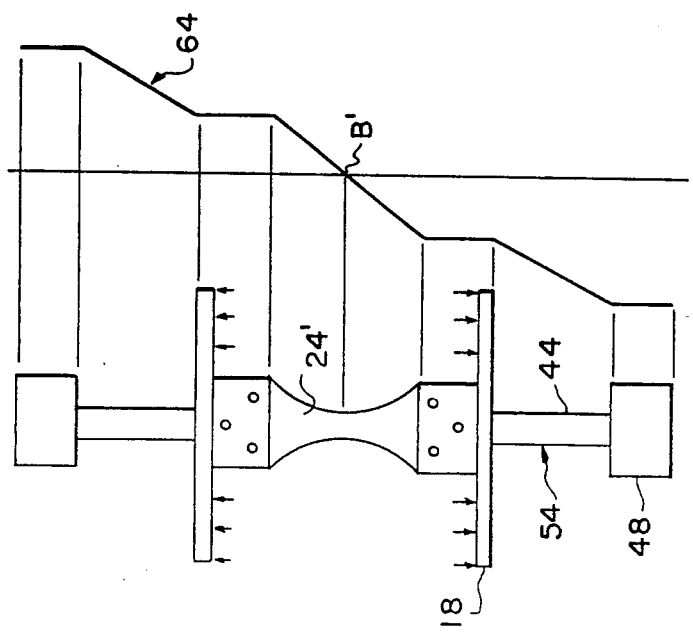
FIG. 2 is a schematic diagram representation of the embodiment of FIG. 1, including a graph of the maximum amplitude of longitudinal vibration of each component of the invention and specimen, set up to perform a crack initiation test.

In the embodiment shown in FIG. 2, the load train 54 is set up to test a specimen 24' for crack initiation studies. In such a system, the shafts and weights are selected such that when shakers 50, 52 (FIG. 1) are actuated to vibrate the load train 54, a single node B' is formed which coincides with the center of the specimen 24', as shown in graph 64, which is a plot of amplitude versus locations along the load train.

With this embodiment the, driving frequency f equals the natural frequency of the load train, and is calculated as follows:

$$\Omega = \frac{f}{f_0} = \left[ \frac{2a + b + 1 - \sqrt{(2a + b + 1)^2 - 8ab}}{2b} \right]^{\frac{1}{2}}$$

where $$a = \frac{k_1}{k_2} \text{ [stiffness ratio]}$$

$$b = \frac{m_1}{m_2} \text{ [mass ratio]}$$

$$f_0 = \frac{1}{2}\pi \sqrt{\frac{k_2}{m_2}}$$

[frequency of resonator (the shaft and weight)]

The variables $k_1$ and $k_2$ are the stiffnesses (spring constants) for the specimen 24', and shaft 44, respectively, and $m_1$ and $m_2$ are the masses of the piston 18 and weight 48, respectively. Since the graph 64 is symmetric about node B' these values would be the same for the components on the opposite side of node B'.

As shown in FIG. 3, proper selection of the weights 46, 48 and shafts 42, 44, for a specific driving frequency from the shakers 50, 52 (FIG. 1) causes the train 54 to vibrate with a pattern of amplitude as shown in the graph 65. In graph 65, there is a node B located at the hole 60 and crack 62 of the specimen 24, which is at the center of the train 54, and there are nodes C and D located along the upper and lower shafts 42, 44 respectively.

It is preferable to select a material and a size for the shafts 42, 44 such that the nodes C, D are closely adjacent to the pistons 16, 18. As a result, the segments of the train 54 extending between B and C and between B and D can be considered to vibrate as a single, isolated component, each having its own stiffness or spring constant.

It is also preferable to select shafts 42, 44 such that the stiffness or spring constant of the segments extending from the pistons 16, 18 to the nodes C, D is relatively large. As shown in FIG. 3, the segments EC and FD are relatively small in length compared to segments BE and BF. These smaller segments will tend to have a very high stiffness when compared to the stiffness of the specimen 24. This is desirable for crack propogation tests since the overall stiffness of the load train segment extending from node C to node B will have to be relatively unaffected by changes in the spring constant of the specimen 24. Thus, addition of appropriate weights to the load train will provide sufficient mass in the load train to minimize natural frequency changes due to distortion of the specimen as the crack propogates.

In selecting the stiffnesses of the shafts 42, 44, and the masses of the pistons 16, 18 and weights 46, 48, it is necessary to first select the desired driving frequency of the shakers 50, 52. The other components can then be selected using the following two alternative formulas:

$$f = \frac{1}{2\pi} \sqrt{\frac{2k_1 + k_{FD}}{m_1}} = \frac{1}{2\pi} \sqrt{\frac{k_{DG}}{m_2}}$$

where f equals the driving frequency, $k_1$ equal the stiffness of the specimen 24, $k_{FD}$ equals the stiffness of the shaft segment between points F and D, $m_1$ equals the mass of the piston 18, $k_{DG}$ equals the stiffness of the shaft segment between points D and G, and $m_2$ equals the mass of the weight 48. Since this system is symmetric about the node B, the formula is the same for selecting the weight 46, shaft 42, and piston 16.

Having described the invention in detail and by reference to preferred embodiments thereof, it will be apparent that modifications and variations are possible without departing from the scope of the invention defined in the appended claims.

What is claimed is:

1. Fatigue testing apparatus comprising: a support frame;

first and second actuators located in spaced aligned relation on said frame;

each of said actuators including
  a cylinder rigidly attached to said frame,
  a piston located in said cylinder,
  flexible diaphragm means attached between said cylinder and said piston,
whereby said cylinder, piston and diaphragm means forms an airtight chamber; and
said piston including a piston rod having a gripping means adapted to be attached to an end of a test specimen;

means for pressurizing said chambers to urge said pistons in opposition to each other to impose a static load on the specimen;

said pistons, rods, and a specimen combining to form a load train which is dynamically isolated from said frame; and driver means for imparting a high frequency vibratory dynamic load to the load train whereby said diaphragms isolate the dynamic load from said cylinders and said frame.

2. The apparatus of claim 1 wherein said actuators are mounted spaced apart to form a vertically aligned load train, and a spring extending between said frame and an upper part of said load train and suspending it from said frame.

3. The apparatus of claim 1 further comprising means for enclosing and heating said specimen and adjacent portions of said piston rods to apply thermal loading to the specimen and allow free thermal expansion of the specimen during testing due to the dynamic isolation of the load train from the frame of the apparatus.

4. The apparatus of claim 1 wherein the specimen and said pistons and rods are selected to form a load train having a natural frequency equal to the frequency imposed by said driver means whereby a node exists along said load train located at a midlength of the specimen.

5. The apparatus of claim 1 including weights attached to said pistons, the mass of said weights together with said pistons being such that the natural frequency of said load train equals the value of high frequency vibrations imposed thereon.

6. The apparatus of claim 5 wherein said rods and weights are sized such that, for a given value of a high frequency driving force imposed thereon, said load train vibrates with a single node adjacent the center of said specimen.

7. The apparatus of claim 5 wherein said rods and weights are sized such that, for a given value of a high frequency driving force imposed thereon, said load train vibrates with a node adjacent the middle of said specimen and with further nodes on said shafts adjacent said pistons.

8. The apparatus of claim 1 wherein said high frequency load imparting means includes a first shaker connected to drive said second piston of the load train.

9. The apparatus of claim 8 wherein said high frequency load imparting means includes a second shaker, connected to said first piston and adjusted to operate 180° out of phase with said first shaker.

10. The apparatus of claim 1 further comprising means for enclosing only said specimen and adjacent portions of said rods of said first and second actuators and for heating said specimen.

11. A high frequency fatigue testing apparatus comprising:
   a support frame;
   a upper actuator including an upper cylinder rigidly attached to said frame and an upper piston forming with said upper cylinder an upper air-tight chamber, said upper piston extending downward from said upper cylinder and having an upper gripping means for attachment to one end of a specimen to be tested;
   supporting means connected between said upper cylinder and said upper piston for decoupling from said upper cylinder vibration imparted to said upper piston:
   a lower actuator including a lower cylinder rigidly attached to said frame and a lower piston forming with said lower cylinder a lower air-tight chamber, said lower piston extending upward from said lower cylinder and having a lower gripping means for attachment to an opposite end of a specimen to be tested;
   supporting means connected between said lower cylinder and said lower piston for decoupling from said lower cylinder vibration imparted to said lower piston;
   means for pressurizing said cylinders to exert a static load on a specimen gripped and supported between said gripping means;
   said upper and lower pistons and said upper and lower gripping means, together with a specimen supported in said gripping means, forming a load train freely movable in said cylinders with respect to said frames and
   flexible suspension means extending between said load train and said frame and supporting said load train for limited free movement with respect to said cylinders and said frame; and
   driver means connected to the load train for vibrating the load train at a predetermined frequency while said suspension means isolates the vibrations from said frame.

12. Fatigue testing apparatus comprising: a support frame;
   first and second actuators located in spaced aligned relation on said frame,
   each of said actuators including
      a cylinder rigidly attached to said frame, a piston supported for free movement in the corresponding said cylinder,
      flexible diaphragm means attached between said cylinder and said piston and supporting said piston for free limited movement within said cylinder while isolating said cylinder from vibration imparted to said piston,
      a piston rod extending from said piston in the direction of the other actuator, and a gripping means on said rod adapted to be attached to opposite ends of a test specimen;
   said pistons, rods, and a specimen mounted therebetween combining to form a load train which is dynamically isolated from said frame; and
   driver means for imparting a vibratory dynamic load to the load train whereby the specimen is subjected to vibratory testing while the dynamic load on said driver means is isolated from said cylinders and said frame.

13. The apparatus of claim 12 further comprising means for enclosing and heating said specimen and adjacent portions of said piston rods to apply thermal loading to the specimen and allow free thermal expansion of the specimen during testing due to the dynamic isolation of the load train from the frame of the apparatus.

14. Testing apparatus as defined in claim 12, wherein said diaphragm means comprises
   a pair of flexible diaphragm members each connected, respectively, at its center to one of said pistons and at its periphery to one of said cylinders to provide support for the corresponding piston and dynamic isolation between the piston and cylinders.

15. A method of fatigue testing a specimen comprising the steps of:
   attaching the specimen to first and second pistons of first and second cylinder actuators fixed to a frame on opposite sides of the specimen, said pistons being movably supported in first and second cylinders of said cylinder actuators and said pistons being vibrationally decoupled from said cylinders
   said pistons and said cylinders also forming first and second airtight chambers therebetween;
   selecting a high frequency dynamic load, then selecting and attaching first and second shafts to said first and second cylinder actuators, respectively, such that a load train consisting of said specimen, pistons and shafts vibrates with a single node located at a midlength of said specimen, at the selected high frequency;
   pressurizing said first and second chambers to impose a static tensile load on the specimen; and
   vibrating the load train at the selected high frequency, thereby imposing the high frequency dynamic load on the specimen but not on the cylinders or frame.

16. The method of claim 15 including adding weights to the load train to provide sufficient mass therein to minimize natural frequency changes in the load train due to distortion of the specimen resulting from crack propogation.

17. The method of claim 16 wherein said selecting step includes selecting said shafts and weights such that said load train vibrates with nodes on said shafts, as well as said single node.

18. The method of claim 17 wherein said selecting step includes selecting said shafts and weights such that said nodes on said shafts are adjacent to said pistons.

19. The method of claim 15 wherein said vibrating step comprises vibrating the load train with a first shaker coupled to one end thereof.

20. The method of claim 19 wherein said vibrating step further comprises vibrating the load train with a second shaker attached to the other end of the load train and driven 180 degrees out of phase with the first shaker.

21. The method of claim 15 further comprising the step of heating the specimen to a predetermined temperature during application of the vibrating force.

* * * * *